US012734269B2

United States Patent

Alvarez Acedo et al.

(12) United States Patent
(10) Patent No.: US 12,734,269 B2
(45) Date of Patent: Sep. 15, 2026

(54) FEMININE HYGIENE ARTICLES AND FILMS SUITABLE FOR USE IN SUCH

(71) Applicant: Dow Global Technologies LLC, Midland, MI (US)

(72) Inventors: Eduardo Alvarez Acedo, Tarragona (ES); Barbara Bonavoglia, Horgen (CH); Michel Brunetto, Sao Paulo (BR); Arkady Krasovskiy, Lake Jackson, TX (US); Andrew Heitsch, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 698 days.

(21) Appl. No.: 18/044,271

(22) PCT Filed: Sep. 15, 2021

(86) PCT No.: PCT/US2021/050483
§ 371 (c)(1),
(2) Date: Mar. 7, 2023

(87) PCT Pub. No.: WO2022/060851
PCT Pub. Date: Mar. 24, 2022

(65) Prior Publication Data

US 2023/0321315 A1 Oct. 12, 2023

(30) Foreign Application Priority Data

Sep. 16, 2020 (EP) .................................... 20382812

(51) Int. Cl.
*A61L 15/58* (2006.01)
*A61F 13/15* (2006.01)
(Continued)

(52) U.S. Cl.
CPC ........ *A61L 15/585* (2013.01); *A61F 13/5514* (2013.01); *A61L 15/225* (2013.01);
(Continued)

(58) Field of Classification Search
CPC ...... A61L 15/585; A61L 15/225; A61L 15/26; A61L 15/24; A61F 13/5514; A61F 2013/15569; C09J 7/401; C09J 7/405
See application file for complete search history.

(56) References Cited

U.S. PATENT DOCUMENTS 3,645,992 A 2/1972 Elston
3,914,342 A 10/1975 Mitchell
(Continued)

FOREIGN PATENT DOCUMENTS

EP 1354575 A1 10/2003
EP 2256173 A1 * 12/2010 ............ B32B 27/32
EP 2574638 A1 9/2017

OTHER PUBLICATIONS

SK Innovation PRIMACOR 3460 datasheet, available at https://sk-fp.com/wp-content/uploads/Technical-datasheet_PRIMACOR-3460_eng_v2.pdf (Year: 2022).*
(Continued)

*Primary Examiner* — Scott R. Walshon
(74) *Attorney, Agent, or Firm* — Dinsmore & Shohl LLP

(57) ABSTRACT

Disclosed herein are feminine hygiene articles and multi-layer film structures. According to one or more embodiments disclosed herein, a feminine hygiene article may include a feminine hygiene pad including an absorbent body, an adhesive layer positioned on at least a surface of the absorbent body, and a pouch wrap in contact with the adhesive layer of the feminine hygiene pad. The pouch wrap may include a release layer in direct contact with the adhesive layer. The release layer may include a polymer
(Continued)

composition including low density polyethylene covalently bonded to polydimethylsiloxane.

13 Claims, 6 Drawing Sheets

(51) Int. Cl.
*A61F 13/551* (2006.01)
*A61L 15/22* (2006.01)
*C09J 7/40* (2018.01)

(52) U.S. Cl.
CPC ............... *C09J 7/401* (2018.01); *C09J 7/405* (2018.01); *A61F 2013/15569* (2013.01)

(56) References Cited

U.S. PATENT DOCUMENTS 4,076,698 A 2/1978 Anderson et al.
4,599,392 A 7/1986 McKinney et al.
5,272,236 A 12/1993 Lai et al.
5,278,272 A 1/1994 Lai et al.
5,476,901 A * 12/1995 Smith .................. C08G 77/442 526/279
5,582,923 A 12/1996 Kale et al.
5,728,469 A 3/1998 Mann et al.
5,733,155 A 3/1998 Sagawa
5,854,045 A 12/1998 Fang et al.
H1935 H * 1/2001 Wilhoit ......................... 428/447
6,239,244 B1 5/2001 Stepp et al.
7,943,120 B2 5/2011 Toyoda et al.
8,292,861 B2 * 10/2012 Toms ................ A61F 13/55185 604/385.03
8,691,923 B2 4/2014 Demirors et al.
9,187,678 B2 11/2015 Boardman et al.
9,527,899 B2 12/2016 Habimana et al.
2008/0299347 A1 12/2008 Ukei et al.
2015/0232706 A1 8/2015 Endo et al.
2018/0098896 A1 * 4/2018 Hardie .................. A61F 13/535

OTHER PUBLICATIONS

Chinese Office Action dated Apr. 23, 2025, pertaining to CN Patent Application No. 202180061816.3, 10 pgs.
International Search Report and Written Opinion dated Dec. 21, 2021, pertaining to Int'l Patent Application No. PCT/US2021/050483, 11 pgs.
Balke et al. "A Strategy for Interpreting Multidetector Size-Exclusion Chromatography Data II", Chromatography of Polymers, Chapter 13, pp. 198-219.
Kratochvil et al. "Fundamental Light-Scattering Methods", Chapter 3, pp. 113-144.
Williams et al. "The Construction of a Polyethylene Calibration Curve for Gel Permeation Chromatography Using Polystyrene Fractions", Polymer Letters, vol. 6, pp. 621-624.
Zimm et al. "Apparatus and Methods for Measurement and Interpretation of the Angular Variation of Light Scattering; Preliminary Results on Polystyrene Solutions", The Journal of Chemcial Physics, vol. 16, No. 12, pp. 1099-1116.
Chinese Office Action dated Nov. 17, 2025, pertaining to CN Patent Application No. 202180061816.3, 12 pgs.

* cited by examiner

FEMININE HYGIENE ARTICLES AND FILMS SUITABLE FOR USE IN SUCH

CROSS-REFERENCE TO RELATED APPLICATIONS

This application is a National Stage Entry under 35 U.S.C. § 371 of International Patent Application No. PCT/US2021/050483, filed Sep. 15, 2021, which claims priority to European Patent Application No. 20382812.4 filed Sep. 16, 2020, the entire disclosures of both of which are incorporated by reference herein.

TECHNICAL FIELD

Embodiments described herein generally relate to polymeric materials and, more specifically, to polymer films which can be used in feminine hygiene articles.

BACKGROUND

Absorbent pads may find use in feminine hygiene applications. These pads usually include an adhesive surface to affix the pad to the undergarments of the end user. These absorbent pads may be individually packaged in a polymeric film referred to as a pouch wrap, and the adhesive surface of the pad usually contacts the pouch wrap. Generally, the end user must remove the feminine hygiene pad from the pouch wrap before use. Thus, there is a need to provide pouch wrap packaging for feminine hygiene products with favorable release properties.

Some pouch wraps used for packaging feminine hygiene pads may include a silicone coating on a surface of the pouch wrap that contacts the adhesive portion of the pad to provide favorable release properties. Applying a silicone coating to the pouch wrap generally includes two additional processing steps of applying the silicone coating and curing the coating.

SUMMARY

Accordingly, a need exists for pouch wrap with favorable release properties that avoids the additional steps of applying and curing a silicone coating. The present disclosure addresses this need and is directed to polymeric materials that may be utilized in pouch wraps of feminine hygiene articles. According to one or more embodiments, a polymer composition comprising low density polyethylene covalently bonded to polydimethylsiloxane may be utilized as a material of a pouch wrap. The polymer may have favorable release properties including low peel force, the force needed to remove the feminine hygiene pad from the pouch wrap. In some embodiments, the release layer includes the polymer as well as support layers. The utilization of the polymer, as opposed to a silicone release layer, may be produced without undergoing the additional processing steps involved in applying and curing the silicone coating. In some embodiments, additional polymer layers may not be needed to support the release film, which may reduce expense as compared with multilayered films used with silicone release layers.

Disclosed herein is a feminine hygiene article. According to one or more embodiments, the feminine hygiene article comprises a feminine hygiene pad comprising an absorbent body and an adhesive layer positioned on at least a surface of the absorbent body; and a pouch wrap in contact with the adhesive layer of the feminine hygiene pad, the pouch wrap comprising a release layer in direct contact with the adhesive layer, the release layer comprising a polymer composition comprising low density polyethylene covalently bonded to polydimethylsiloxane.

Also disclosed herein is a multilayer film structure. According to one or more embodiments, the multilayer film structure comprises one or more support layers comprising polymers; and a release layer in direct contact with a support layer, the release layer comprising a polymer composition comprising ethylene and (meth)acrylic ester functionalized polydimethylsiloxane copolymers.

These and other embodiments are described in more detail in the following Detailed Description and the Drawings.

BRIEF DESCRIPTION OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1A:
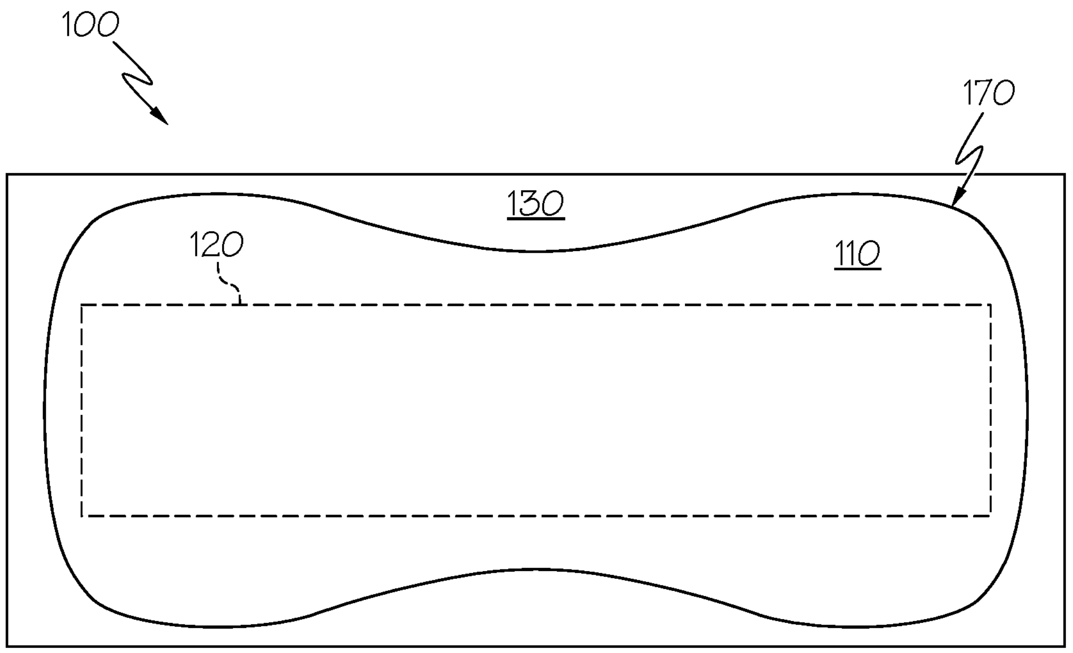
FIG. 1A schematically depicts an overhead view of a feminine hygiene article, according to one or more embodiments disclosed herein.

Reference will now be made in greater detail to various embodiments, some embodiments of which are illustrated in the accompanying drawings. Whenever possible, the same reference numerals will be used throughout the drawings to refer to the same or similar parts.

Definitions

The term “composition,” as used herein, refers to a mixture of materials that comprises the composition, as well as reaction products and decomposition products formed from the materials of the composition.

The terms “comprising,” “including,” “having,” and their derivatives, are not intended to exclude the presence of any additional component, step or procedure, whether or not the same is specifically disclosed. In order to avoid any doubt, all compositions claimed through use of the term "comprising" may include any additional additive, adjuvant, or compound, whether polymeric or otherwise, unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed.

The term "polymer" refers to a polymeric compound prepared by polymerizing monomers, whether of a same or a different type. The generic term polymer thus embraces the term "homopolymer," which usually refers to a polymer prepared from only one type of monomer as well as "copolymer," which refers to a polymer prepared from two or more different monomers. The term "interpolymer," as used herein, refers to a polymer prepared by the polymerization of at least two different types of monomers. The generic term interpolymer thus includes a copolymer or polymer prepared from more than two different types of monomers, such as terpolymers.

"Blend," "polymer blend," and like terms mean a composition of two or more polymers. Such a blend may or may not be miscible. Such a blend may or may not be phase separated. Such a blend may or may not contain one or more domain configurations, as determined from transmission electron spectroscopy, light scattering, x-ray scattering, and any other suitable method. Blends are not laminates, but one or more layers of a laminate may contain a blend. Such blends can be prepared as dry blends, formed in situ (e.g., in a reactor), melt blends, or using other techniques known to those of skill in the art.

"Polyethylene" or "ethylene-based polymer" shall mean polymers comprising greater than 50% by mole of units derived from ethylene monomer. This includes ethylene-based homopolymers or copolymers (meaning units derived from two or more comonomers). Common forms of ethylene-based polymers known in the art include, but are not limited to, Low Density Polyethylene (LDPE); Linear Low Density Polyethylene (LLDPE); Ultra Low Density Polyethylene (ULDPE); Very Low Density Polyethylene (VLDPE); single-site catalyzed Linear Low Density Polyethylene, including both linear and substantially linear low density resins (m-LLDPE); Medium Density Polyethylene (MDPE); and High Density Polyethylene (MDPE).

"Polypropylene" or "propylene-based polymer" as used herein, refers to a polymer that comprises, in polymerized form, greater than 50% by mole of units that have been derived from propylene monomer. This includes propylene homopolymer, random copolymer polypropylene, impact copolymer polypropylene, and propylene/α-olefin copolymer.

The term "LDPE" may also be referred to as "high pressure ethylene polymer" or "highly branched polyethylene" and is defined to mean that the polymer is partly or entirely homopolymerized or copolymerized in autoclave or tubular reactors at pressures above 14,500 psi (100 MPa) with the use of free-radical initiators, such as peroxides (see, for example, U.S. Pat. No. 4,599,392, which is hereby incorporated by reference in its entirety). LDPE resins typically have a density in the range of 0.916 g/cm$^3$ to 0.940 g/cm$^3$.

The term "LLDPE" includes resin made using Ziegler-Natta catalyst systems as well as resin made using single-site catalysts, including, but not limited to, bis-metallocene catalysts (sometimes referred to as "m-LLDPE"), phosphinimine, and constrained geometry catalysts, and resins made using post-metallocene, molecular catalysts, including, but not limited to, bis(biphenylphenoxy) catalysts (also referred to as polyvalent aryloxyether catalysts). LLDPE includes linear, substantially linear, or heterogeneous ethylene-based copolymers or homopolymers. LLDPEs contain less long chain branching than LDPEs and include the substantially linear ethylene polymers, which are further defined in U.S. Pat. Nos. 5,272,236, 5,278,272, 5,582,923 and 5,733,155 each of which are incorporated herein by reference in their entirety; the homogeneously branched linear ethylene polymer compositions such as those in U.S. Pat. No. 3,645,992 which is incorporated herein by reference in its entirety; the heterogeneously branched ethylene polymers such as those prepared according to the process disclosed in U.S. Pat. No. 4,076,698 which is incorporated herein by reference in its entirety; and blends thereof (such as those disclosed in U.S. Pat. Nos. 3,914,342 and 5,854,045 which are incorporated herein by reference in their entirety. The LLDPE resins can be made via gas-phase, solution-phase, or slurry polymerization or any combination thereof, using any type of reactor or reactor configuration known in the art.

The term "MDPE" refers to polyethylenes having densities from 0.917 g/cm$^3$ to 0.936 g/cm$^3$. MDPE is typically made using chromium or Ziegler-Natta catalysts or using single-site catalysts including, but not limited to, substituted mono- or bis-cyclopentadienyl catalysts (typically referred to as metallocene), constrained geometry catalysts, phosphinimine catalysts and polyvalent aryloxyether catalysts (typically referred to as bisphenyl phenoxy).

The term "MDPE" refers to polyethylenes having densities greater than 0.935 g/cm$^3$ and up to 0.980 g/cm$^3$, which are generally prepared with Ziegler-Natta catalysts, chrome catalysts or single-site catalysts including, but not limited to, substituted mono- or bis-cyclopentadienyl catalysts (typically referred to as metallocene), constrained geometry catalysts, phosphinimine catalysts & polyvalent aryloxyether catalysts (typically referred to as bisphenyl phenoxy).

The term "ULDPE" refers to polyethylenes having densities of 0.855 g/cm$^3$ to 0.912 g/cm$^3$, which are generally prepared with Ziegler-Natta catalysts, chrome catalysts, or single-site catalysts including, but not limited to, substituted mono- or bis-cyclopentadienyl catalysts (typically referred to as metallocene), constrained geometry catalysts, phosphinimine catalysts & polyvalent aryloxyether catalysts (typically referred to as bisphenyl phenoxy). ULDPEs include, but are not limited to, polyethylene (ethylene-based) plastomers and polyethylene (ethylene-based) elastomers. Polyethylene (ethylene-based) elastomers plastomers generally have densities of 0.855 g/cm$^3$ to 0.912 g/cm$^3$.

"Multilayer structure" or "multilayer film" means any structure having more than one layer. For example, the multilayer structure (for example, a film) may have two, three, four, five, six, seven, or more layers.

As used herein, "direct contact" means that there may not be any other layers positioned between the two layers that are in direct contact with one another.

Feminine Hygiene Article

Figure 1B:
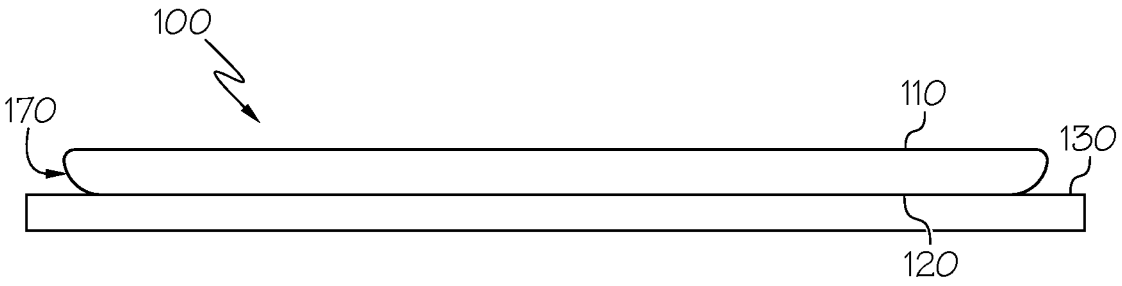
FIG. 1B schematically depicts a side view of a feminine hygiene article, according to one or more embodiments disclosed herein.

The structure and properties of feminine hygiene articles according to various embodiments are described herein. As shown in FIGS. 1A and 1B, in one or more embodiments, a feminine hygiene article 100 may comprise a feminine hygiene pad 170 and a pouch wrap 130. FIG. 1A provides a top view of a feminine hygiene article according to one or more embodiments, and FIG. 1B provides a side view of a feminine hygiene article according to one or more embodiments. In one or more embodiments, the feminine hygiene pad 170 may be in direct contact with pouch wrap 130.

According to one or more embodiments, a feminine hygiene pad 170 may comprise an absorbent body 110 and an adhesive layer 120. The absorbent body 110 may comprise any suitable absorbent material for use in feminine hygiene applications. The adhesive layer 120 may comprise any suitable adhesive for use in feminine hygiene pads. In one or more embodiments, the adhesive may be any adhesive suitable to affix the feminine hygiene pad to an article of clothing during its end use.

Figure 2:
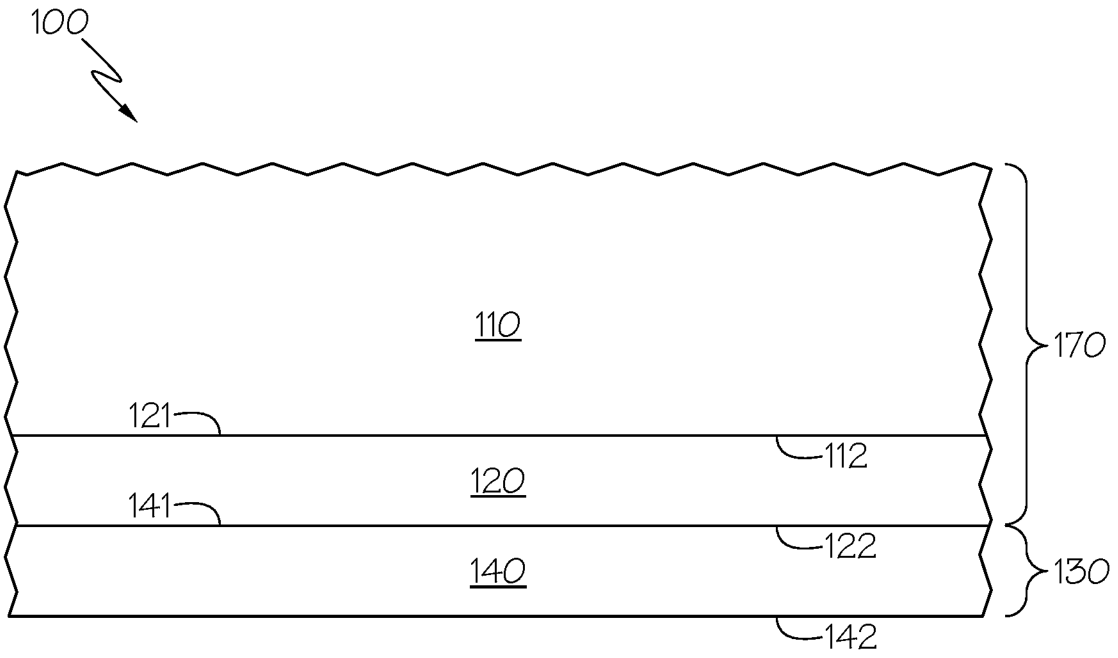
FIG. 2 schematically depicts a cross sectional view of a portion of a feminine hygiene article, according to one or more embodiments disclosed herein.

Referring to FIGS. 1A and 1B, the adhesive layer 120 may be positioned on at least a portion of a surface of the absorbent body 110. As shown in FIG. 2, the adhesive layer 120 may be in direct contact with the absorbent body 110. The direct contact between adhesive layer 120 and absorbent body 110 may occur at surface 121 of the adhesive layer 120. In one or more embodiments, the adhesive layer 120 may be positioned between the absorbent body 110 and the pouch wrap 130. The adhesive layer may be in direct contact with the pouch wrap 130. The direct contact between adhesive layer 120 and pouch wrap 130 may occur at surface 122 of the adhesive layer 120. In one or more embodiments, the adhesive layer 120 may be in direct contact with both the absorbent body 110 at surface 121 of the adhesive layer 120 and the pouch wrap 130 at surface 122 of the adhesive layer 120.

Referring now to FIG. 2, a cross-section view of feminine hygiene article 100 is depicted. The absorbent body 110 may comprise a surface 112. The adhesive layer 120 may comprise a top surface 121 and a bottom surface 122. The adhesive layer 120 may generally have a planar geometry where the top surface 121 is opposite the bottom surface 122. The pouch wrap 130 may comprise, consist essentially of, or consist of a release layer 140. The release layer 140 may comprise a top surface 141 and a bottom surface 142. The release layer may have a generally planar geometry where the top surface 141 is opposite the bottom surface 142. The bottom surface 142 of the release layer 140 may be an air-side surface, defining the edge of the pouch wrap 130. When the feminine hygiene pad 170 is pulled away from the pouch wrap 130, the top surface 141 of the release layer 140 may be an air-side surface, and the bottom surface 122 of the adhesive layer 120 may be affixed to an undergarment of an end user.

In embodiments, the entirety of the pouch wrap 130 may be a single film layer (i.e., the release layer 140). In such embodiments, the bottom surface 142 of the release layer 140 may be an air-side surface, defining the edge of the pouch wrap 130. In embodiments, the adhesive layer 120 may be positioned between the absorbent pad 110 and the release layer 140. In one or more embodiments, the release layer 140 may be in direct contact with the feminine hygiene pad 170. Direct contact of the release layer 140 and the feminine hygiene pad 170 may occur when the bottom surface 122 of the adhesive layer 120 is adjacent to the top surface 141 of the release layer 140.

Figure 3:
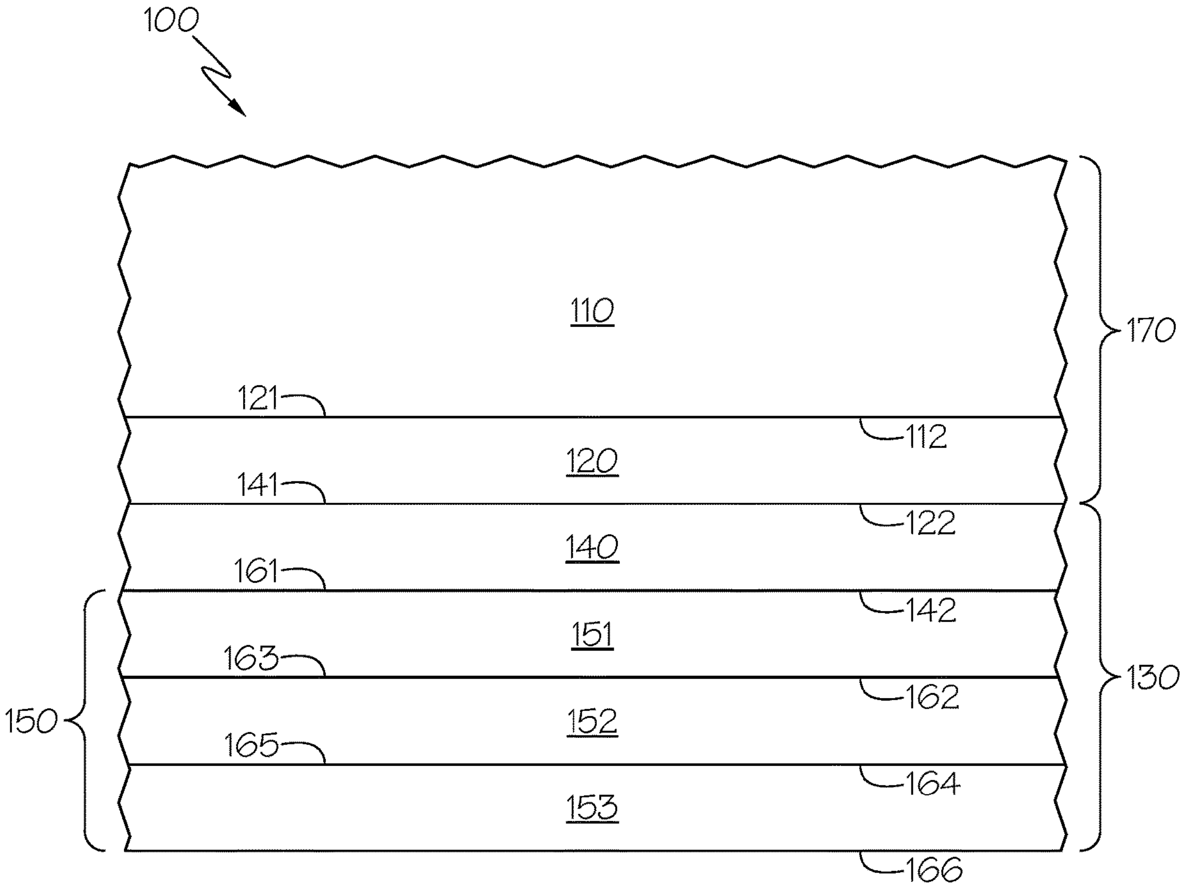
FIG. 3 schematically depicts a cross sectional view of a portion of a feminine hygiene article including a multilayer film pouch wrap, according to one or more embodiments disclosed herein.

Referring now to FIG. 3, a cross-sectional view of feminine hygiene article 100 is depicted. In embodiments, the pouch wrap 130 may be a multilayer film. The multilayer film may comprise a release layer 140 and one or more support layers 150. In one or more embodiments, the release layer 140 may be positioned between the adhesive layer 120 and the support layers 150. The release layer 140 may be in direct contact with the support layers 150.

As shown in FIG. 3, the pouch wrap 130 may comprise a release layer 140 and three support layers 150, including a first support layer 151, a second support layer 152, and a third support layer 153. The first support layer may have a top surface 161 and a bottom surface 162. The first support layer may have a substantially planar geometry where the top surface 161 is opposite the bottom surface 162. The first support layer 151 may be positioned between release layer 140 and the second support layer 152. The top surface 161 of the first support layer may be in direct contact with the bottom surface 142 of release layer 140.

The second support layer 152 may have a top surface 163 and a bottom surface 164. The second support layer may have a substantially planar geometry where the top surface 163 is opposite the bottom surface 164. The second support layer 152 may be positioned between the first support layer 151 and the third support layer 153. The top surface 163 of the second support layer may be in direct contact with the bottom surface 162 of the first support layer 151.

The third support layer 153 may have a top surface 165 and a bottom surface 166. The third support layer may have a substantially planar geometry where the top surface 165 is opposite the bottom surface 166. The top surface 165 of the third support layer 153 may be in direct contact with the bottom surface 164 of the second support layer 152. Additionally, the bottom surface 166 of the third release layer 153 may be an air-side surface and may define an edge of the pouch wrap 130.

In one or more embodiments, the release layer 140 may comprise from 5 wt % to 20 wt % of the pouch wrap 130. For example, the release layer 140 may comprise from 5 to 20 wt %, from 6 to 20 wt %, from 7 to 20 wt %, from 8 to 20 wt %, from 9 to 20 wt %, from 10 to 20 wt %, from 11 to 20 wt %, from 12 to 20 wt %, from 13 to 20 wt %, from 14 to 20 wt %, from 15 to 20 wt %, from 16 to 20 wt %, from 17 to 20 wt %, from 18 to 20 wt %, or even from 19 to 20 wt % of the pouch wrap 130. In further examples, the release layer 140 may comprise from 5 to 19 wt %, from 5 to 18 wt %, from 5 to 17 wt %, from 5 to 16 wt %, from 5 to 15 wt %, from 5 to 14 wt %, from 5 to 13 wt %, from 5 to 12 wt %, from 5 to 11 wt %, from 5 to 10 wt %, from 5 to 9 wt %, from 5 to 8 wt %, from 5 to 7 wt %, or even from 5 to 6 wt % of the pouch wrap 130.

The support layers 150 may comprise one or more polymers. In embodiments, the support layers may comprise one or more blends of polymers. In embodiments, the support layers may comprise polyethylene, polypropylene, or combinations thereof. In further embodiments, the support layers may comprise LDPE, LLDPE, MDPE, MDPE, ULDPE, or combinations thereof.

In one or more embodiments, the pouch wrap 130 may have a basis weight from 5 to 40 gsm (grams per square meter). For example, the pouch wrap may have a basis weight from 5 to 40 gsm, from 5 to 35 gsm, from 5 to 30 gsm, from 5 to 25 gsm, from 5 to 20 gsm, or even from 5 to 15 gsm. In further examples, the pouch wrap 130 may have a basis weight from 10 to 40 gsm, from 20 to 40 gsm, from 25 to 40 gsm, from 30 to 40 gsm, or even from 35 to 40 gsm. In one or more preferred embodiments, the pouch wrap 130 may have a basis weight from 12 to 18 gsm.

In one or more embodiments, the pouch wrap 130 may be void of any material comprising at least 60 wt % silicone resins. For example, the pouch wrap 130 may be void of any material comprising at least 60 wt %, at least 70 wt %, at least 80 wt %, at least 90 wt %, or even at least 99 wt % silicone resins. In further embodiments, the pouch wrap 130 may be void of a layer consisting essentially of, or consisting of silicone resins. As described herein, "silicone resins" refers to siloxane polymers comprising at least 60 wt % siloxane monomers. As described herein, "silicone resins" do not refer to polymer compositions comprising low density polyethylene covalently bonded to polydimethylsiloxane, as described in more detail subsequently herein.

In further embodiments, the pouch wrap 130 may comprise 1, 2, 3, 4, 5, 6, 7, 8, or more support layers. For example, the pouch wrap may comprise 2 to 8, 2 to 7, 2 to 6, 2 to 5, 2 to 4, or even 2 to 3 support layers. In further examples, the pouch wrap may comprise 3 to 8, 4 to 8, 5 to 8, 6 to 8, or even 7 to 8 support layers.

It should be understood that any of the release layer and support layers may further comprise one or more additives as known to those of skill in the art such as, for example, plasticizers, stabilizers including viscosity stabilizers, hydrolytic stabilizers, primary and secondary antioxidants, ultraviolet light absorbers, anti-static agents, dyes, pigments or other coloring agents, inorganic fillers, fire-retardants, lubricants, reinforcing agents such as glass fiber and flakes, synthetic (for example, aramid) fiber or pulp, foaming or blowing agents, processing aids, slip additives, antiblock agents such as silica or talc, or combinations of two or more thereof. Inorganic fillers, such as calcium carbonate, and the like can also be incorporated into one or more of the release layer and support layers. In some embodiments, the release layer and support layers may each include up to 25 weight percent of such additional additives based on the total weight of the respective layer. All individual values and subranges from 0 wt % to 25 wt % are included and disclosed herein; for example, the total amount of additives in the release layer or each of the support layers can be from 0.5 wt % to 25 wt %, from 0.5 wt % to 20 wt %, from 0.5 wt % to 15 wt %, from 0.5 wt % to 10 wt %, from 0.5 wt % to 5 wt %, from 0.5 wt % to 1 wt %, from 1 wt % to 25 wt %, from 5 wt % to 25 wt %, from 10 wt % to 25 wt %, from 15 wt % to 25 wt %, or from 20 wt % to 25 wt %, based on the total weight of the respective layer. The incorporation of the additives can be carried out by any known process such as, for example, by dry blending, by extruding a mixture of the various constituents, by the conventional master batch technique, or the like.

In one or more embodiments, the feminine hygiene article may comprise a nonwoven fabric layer. As described herein, a "nonwoven fabric" refers to a fabric made of short and long fibers that are bonded together by a chemical, mechanical, heat, or solvent treatment. Nonwoven fabric may be fabric that is produced by neither weaving nor knitting. In one or more embodiments, the pouch wrap may be positioned between the adhesive layer and the nonwoven fabric. The nonwoven fabric may be in direct contact with the pouch wrap. In further embodiments, the support layers may be positioned between the release layer and the nonwoven fabric. In embodiments, the nonwoven fabric may be in direct contact with a support layer. For example, the nonwoven layer may be in direct contact with the bottom surface 166 of support layer 153 depicted in FIG. 3.

In one or more embodiments, the maximum peel force required to remove the feminine hygiene pad from the release layer of the pouch wrap is at most 7.0 N/25 mm. As described herein, "peel force" refers to the force required to remove an adhesive from a surface. Peel force may be measured by any suitable means. The maximum peel force required to remove the feminine hygiene pad from the release layer refers to the largest amount of force required to remove the feminine hygiene pad at any point during the removal process. For example, the maximum peel force may be at most 7.0 N/25 mm, at most 6.5 N/25 mm, at most 6.0 N/25 mm, at most 5.5 N/25 mm, at most 5.0 N/25 mm, at most 4.5 N/25 mm, or even at most 4.0 N/25 mm.

As described herein, the "coefficient of friction" refers to a dimensionless scalar value that describes the ratio of the force of friction between two bodies and the force pressing them together. The static coefficient of friction refers to the coefficient of friction when the bodies are stationary with respect to each other and the dynamic coefficient of friction refers to the coefficient of friction when the bodies are in motion with respect to each other. Static and dynamic coefficients of friction of a plastic film sliding along itself may be measured according to ISO-8295 among other suitable methods.

In one or more embodiments, the static coefficient of friction of the release layer in contact with itself is at most 0.55. In embodiments, the static coefficient of friction of the release layer in contact with itself is at most 0.55, at most 0.52, at most 0.50, at most 0.47, at most 0.45, at most 0.42, or even at most 0.40. In one or more embodiments, the dynamic coefficient of friction of the release layer in motion with respect to itself is at most 0.60. For example, the dynamic coefficient of friction of the release layer in motion with respect to itself is at most 0.60, at most 0.55, at most 0.50, at most 0.45, at most 0.40, at most 0.35, or even at most 0.30.

The composition and properties of the release layer are further discussed herein. In one or more embodiments, the release layer may comprise a polymer composition comprising low density polyethylene covalently bonded to polydimethylsiloxane. In one or more embodiments, the polymer composition may comprise the reaction product of the copolymerization of ethylene and (meth)acrylic ester functionalized polydimethylsiloxane. Such embodiments are referred to as "copolymer embodiments" and are described in further detail subsequently herein. In one or more embodiments, the polymer composition may comprise low density polyethylene covalently bonded to one or more methyl groups of the polydimethylsiloxane. Such embodiments are referred to as "grafted polymer embodiments" and are described in further detail subsequently herein. It should be understood that both the copolymer embodiments and grafted embodiments may be polymer compositions comprising low density polyethylene covalently bonded to polydimethylsiloxane, as is describe herein.

Copolymer Embodiments

In one or more embodiments, the release layer may comprise copolymers of ethylene and functionalized polysiloxane. In embodiments, the copolymers are formed by high pressure, free-radical polymerization by reacting ethylene monomer and functionalized polysiloxane, sometimes referred to herein as f-PDMS, or by reacting ethylene monomer and a mixture of functionalized polysiloxanes. In one or more embodiments, polydimethylsiloxane (PDMS) is attached to the high pressure ethylene polymer via several covalent bonds that are resulting from the reaction of the initial function of the functionalized PDMS with propagating chain of the ethylene polymer followed up by further reaction with ethylene monomers and also includes bridge between functional group that gets polymerized and siloxane. An embodiment of the copolymer comprising ethylene monomer and (meth)acrylic ester functionalized polydimethylsiloxane is referred to herein as PDMS-co-LDPE.

In one or more embodiments, the PDMS-co-LDPE may include from 0.1 wt % to 50 wt % of PDMS, such as from 0.1 wt % to 20 wt %, from 0.5 wt % to 20 wt %, from 2.0 wt % to 20 wt %, from 2.0 wt % to 15 wt %, from 2.0 wt % to 12 wt %, from 2.0 wt % to 10 wt %, from 1.0 wt % to 10 wt %, from 5.0 wt % to 10 wt %, or from 5.0 wt % to 20 wt %, based on a total weight of the PDMS-co-LDPE composition which also includes LDPE formed during copolymerization but not covalently attached to PDMS and may also include some amount of unreacted f-PDMS.

In various embodiments, the copolymer comprises, but is not limited to, one or more of the following structures:

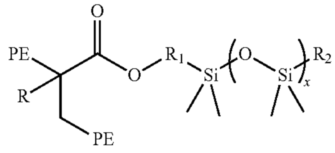

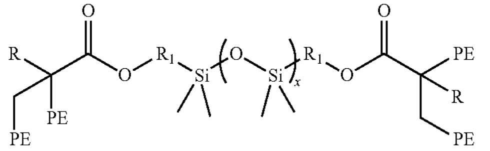

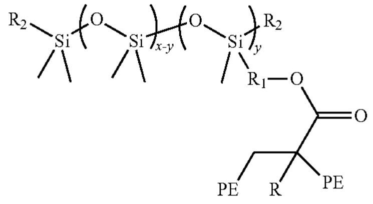

where R is methyl or hydrogen, $R^1$ is a bridge group that connects functional group ((meth)acrylate) with siloxane, $R^2$ is an end group selected from the group consisting of alkyl, substituted alkyl, aryl, alkenyl, H, and OH, x is an integer from 10 to 1000, and y is an integer from 1 to 20. $R^1$ and $R^2$ groups can be the same or different.

In one or more embodiments, the bridge group of the PDMS-co-LDPE is selected from substituted or unsubstituted $C_2$-$C_{20}$ alkylene linker where one or more carbon atoms can be substituted with oxygen and/or silicon, a substituted or unsubstituted aryl group, and derivatives and combinations thereof. In embodiments, the functional group bound to the bridge group is bound to the high pressure ethylene polymer by means of copolymerization with ethylene monomer. In various embodiments, the functional group is a (meth)acrylate ester group. In further embodiments, the bridge group is the group depicted below:

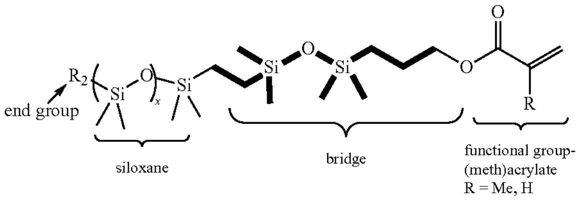

In the structural formulas above, the ethylene-based polymeric branch is depicted as being a polyethylene (PE), but it is contemplated that, in embodiments, the ethylene-based polymeric branch can be a homopolymer (e.g., LDPE) or a copolymer, such as, for example, an ethylene (meth)acrylic ester copolymer, or ethylene (meth)acrylic acid copolymer, or ethylene vinyltrimethoxysilane copolymer, or ethylene vinyl acetate copolymer.

In one or more embodiments, the polymer comprises a polysiloxane unit, which in embodiments, is derived from functionalized polydimethylsiloxane (e.g., f-PDMS). In one or more embodiments, the functionalized polysiloxane is a (meth)acrylate ester functionalized polymethyldisiloxane (f-PDMS), where (meth)acrylate function attached to the PDMS via a bridge.

The polysiloxane may be any of a diverse class of polymers manufactured as fluids, resins, or elastomers. Polysiloxanes are partially organic compounds, but, unlike most polymers, they have a backbone containing no carbon, composed instead of alternating silicon and oxygen atoms, as shown above. Although in the structural formulas shown above, each silicon is illustrated as being bound to a methyl and/or R groups, it is contemplated that each of those positions can individually be an alkyl, vinyl, phenyl, hydrogen, hydroxyl, acetoxy, enoxy, oxime, methoxy, ethoxy, alkoxy, dimethylamino, aminopropyl, hydroxypropyl, mercaptopropyl, chloropropyl, acryloxyprogpyl, methacryloxypropyl, epoxypropoxypropyl, or epoxycyclohexylethyl. In embodiments, each position is methyl.

In one or more embodiments, x is sufficiently large such that the polysiloxane has a viscosity of 100 or more, 200 or more, or 500 or more, centistokes (CST). In embodiments, x is no larger than would produce a polysiloxane with a viscosity no greater than 2.5 million CST. However it is contemplated that the upper limit on the viscosity is lower than 2.5 million CST, for example, 1 million or 600,000 CST.

Polysiloxanes suitable for use in various embodiments include those described in U.S. Pat. No. 6,239,244, the entire contents of which is hereby incorporated by reference in its entirety. The polysiloxanes are commercially available from a number of different manufacturers including, but not limited to Dow, Momentive, Wacker, Shin-Etsu, and Evonik.

In various embodiments described herein, the polysiloxane is a polydimethylsiloxane (PDMS) that includes one or more functional groups and is, therefore, referred to a functionalized PDMS, or f-PDMS. In various embodiments, the f-PDMS is a (meth)acrylate ester functionalized PDMS, where the (meth)acrylate ester group is bonded to the PDMS through a bridge group. The PDMS may be monofunctional or difunctional or polyfunctional, and the functional group(s) may be linked at a terminal or pendant location on the siloxane. Accordingly, in embodiments, the f-PDMS comprises one of the following structures or combinations thereof:

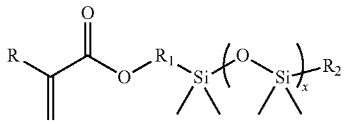

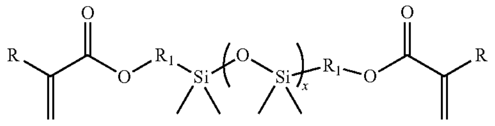

-continued

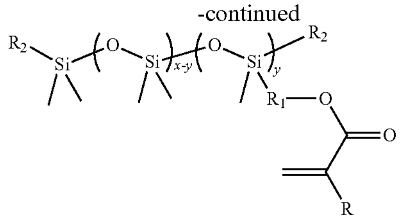

where R is a methyl group or a hydrogen, $R^1$ is a bridge group, $R^2$ is an end group selected from alkyl, aryl, alkenyl, H, or OH, x is an integer from 10 to 1000, and y is an integer from 1 to 20.

In one or more embodiments, the PDMS-co-LDPE may have a polydispersity index (PDI) of from 3.0 to 50.0, such as from 3.0 to 45.0, from 3.0 to 40.0, from 3.0 to 35.0, from 3.0 to 30.0, from 3.0 to 20.0, or from 5.0 to 20.0. In one or more embodiments, the PDMS-co-LDPE may have a melt index ($I_2$) of from 0.1 to 1000.00 g/10 min, from 0.15 to 500.00 g/10 min, such as from 0.15 to 100.00 g/10 min, from 0.15 to 25.00 g/10 min, from 0.15 to 10.00 g/10 min, from 0.50 to 10.00 g/10 min, or from 0.50 to 7.50 g/10 min.

Grafted Polymer Embodiment

In one or more embodiments, the release layer may comprise a polymer composition comprising low density polyethylene covalently bonded to the polydimethylsiloxane by one or more $CH_2$ groups, wherein the one or more $CH_2$ groups are former methyl groups of the polydimethylsiloxane. Such polymers are described in detail in U.S. Pat. No. 8,691,923, the entirety of which is incorporated by reference herein. Additionally, such polymers may be referred to as PDMS-g-LDPE. The low density polyethylene may be formed directly on the polydimethylsiloxane or may be formed independently and subsequently grafted to the polydimethylsiloxane. In one or more embodiments, the polydimethylsiloxane may comprise one or more ethylene-based polymer branches. The number of branches on any polydimethylsiloxane is a function, at least in part, of the size of the siloxane and the conditions under which the ethylene is polymerized or the polyethylene is grafted to the siloxane. The ethylene based polymer branches may attach to the polydimethylsiloxane at the methyl groups of the polydimethylsiloxane, as such a methyl group may relinquish a hydrogen atom to become a $CH_2$ group bound to a low density polyethylene. As such, these $CH_2$ groups may be referred to as former methyl groups of the polydimethylsiloxane.

In embodiments, the PDMS-g-LDPE has a density from 0.91 g/cc to 0.99 g/cc. For example, the PDMS-g-LDPE may have a density from 0.91 g/cc to 0.99 g/cc, from 0.92 g/cc to 0.96 g/cc, from 0.93 g/cc to 0.96 g/cc, from 0.94 g/cc to 0.96 g/cc, or even from 0.95 g/cc to 0.96 g/cc. In further examples, the PDMS-g-LDPE may have a density from 0.91 g/cc to 0.99 g/cc, from 0.91 g/cc to 0.95 g/cc, from 0.91 g/cc to 0.94 g/cc, from 0.91 g/cc to 0.93 g/cc, or even from 0.91 g/cc to 0.92 g/cc.

In embodiments, the PDMS-g-LDPE may have a melt index (MI) ($I_2$) from 0.01 to 1000 g/10 min. For example, the PDMS-g-LDPE may have a MI ($I_2$) from 0.01 to 250 g/10 min, from 0.05 to 250 g/10 min, from 0.10 to 250 g/10 min, from 0.5 to 50 g/10 min, from 1.0 to 25 g/10 min, from 2.0 to 25 g/10 min, from 3.0 to 25 g/10 min, from 4.0 to 25 g/10 min, from 5.0 to 25 g/10 min, from 10 to 25 g/10 min, or even from 15 to 25 g/10 min. In further examples, the PDMS-g-LDPE may have a MI ($I_2$) from 0.01 to 25 g/10 min, from 0.01 to 15 g/10 min, from 0.01 to 10 g/10 min, from 0.01 to 5.0 g/10 min, from 0.01 to 4.0 g/10 min, from 0.01 to 3.0 g/10 min, from 0.01 to 2.0 g/10 min, from 0.01 to 1.0 g/10 min, from 0.01 to 0.5 g/10 min, from 0.01 to 0.1 g/10 min, or even from 0.01 to 0.05 g/10 min.

In embodiments, the PDMS-g-LDPE may have a viscosity at 25° C. from 100 cSt to 20,000 cSt. For example, the PDMS-g-LDPE may have a viscosity at 25° C. from 100 cSt to 20,000 cSt, from 200 cSt to 20,000 cSt, from 500 cSt to 20,000 cSt, from 1,000 cSt to 20,000 cSt, from 5,000 cSt to 20,000 cSt, from 10,000 cSt to 20,000 cSt, or even from 15,000 cSt to 20,000 cSt. In further examples, the PDMS-g-LDPE may have a viscosity at 25° C. from 100 cSt to 15,000 cSt, from 100 cSt to 10,000 cSt, from 100 cSt to 5,000 cSt, from 100 cSt to 1,000 cSt, from 100 cSt to 500 cSt, or even from 100 cSt to 200 cSt.

In embodiments, the PDMS-g-LDPE comprises from 1 wt % to 50 wt % PDMS and a reciprocal amount of LDPE, from 99 wt % to 50 wt %. For example, the PDMS-g-LDPE may comprise from 20 wt %, 22 wt %, 24 wt %, 25 wt %, 30 wt %, 35 wt %, 40 wt %, or even 45 wt % to 50 wt % PDMS; and a reciprocal amount of LDPE, including from 80 wt %, 78 wt %, 76 wt %, 75 wt %, 70 wt %, 65 wt %, 60 wt %, or even 55 wt %, to 50 wt % LDPE. Additionally, in one or more embodiments, the PDMS-g-LDPE includes PDMS that is not covalently bonded to LDPE. The PDMS not covalently bonded to LDPE may be removed from the PDMS-g-LDPE by various suitable purification methods, including but not limited to solvent extraction.

Unless stated to the contrary, implicit from the context, or customary in the art, all parts and percents are based on weight and all test methods are current as of the filing date of this disclosure.

Test Methods

Density

Density is measured in accordance with ASTM D792, Method B. The result is recorded in grams per cubic centimeter (g/cc).

Melt Index

Melt index (MI) ($I_2$), in grams eluted per 10 minutes (g/10 min), is measured using ASTM D1238 (190° C./2.16 kg). $I_{10}$ is measured in accordance with ASTM D1238 (190° C./10 kg), and is reported in g/10 min.

Viscosity

Viscosities up to 100,000 centistokes (cSt) are measured in accordance with ASTM D-445, IP 71 (at 25° C., constant temperature water bath, equilibration time at least 15 minutes) using a glass capillary viscometer, such as an Ubbelohde viscometer.

DSC Crystallinity

Differential scanning calorimetry (DSC) can be used to measure the crystallinity of a sample at a given temperature for a wide range of temperatures. For the examples, a TA model Q1000 DSC (TA Instruments, New Castle, DE) equipped with an RCS (refrigerated cooling system) cooling accessory and an auto-sampler module was used to perform the tests. During testing, a nitrogen purge gas flow of 50 mL/min was used. Resins were compression-molded into 3 mm thick by 1 inch circular plaques at 350° C. for 5 minutes under 1500 psi pressure in air. The sample was then taken out of the press and placed on a counter top to cool to room temperature (approximately 25° C.). A 3-10 mg sample of the cooled material was cut into a 6 mm diameter disk, weighed, placed in a light aluminum pan, and crimped shut. The sample was then tested for its thermal behavior.

The thermal behavior of the sample was determined by changing the sample temperature upwards and downwards to create a response versus temperature profile. The sample was first rapidly heated to 180° C. and held at an isothermal state for 3 minutes in order to remove any previous thermal history. Next, the sample was cooled to −40° C. at a 10° C./min cooling rate and held at −40° C. for 3 minutes. The sample was then heated to 150° C. at a 10° C./min heating rate. The cooling and second heating curves were recorded. The values determined were peak melting temperature ($T_m$), peak crystallization temperature ($T_c$), heat of fusion ($H_f$) (in J/g), and the calculated percent crystallinity for polyethylene samples using the following Equation 1:

$$\%\ \text{crystallinity} = \frac{H_f}{292\ \text{J/g}} \times 100 \qquad \text{(Eq. 1)}$$

The heat of fusion ($H_f$) and the peak melting temperature are reported from the second heat curve. Peak crystallization temperature was determined from the cooling curve.

Gel Permeation Chromatography (GPC)

The GPC system consists of a PolymerChar GPC-IR (Valencia, Spain) high temperature GPC chromatograph equipped with an internal IR5 infra-red detector (IR5) and 4-capillary solution viscometer (DV) coupled to a Precision Detectors (now Agilent Technologies, Amherst, MA) 2-angle light scattering (LS) detector Model 2040. A GPC with the last two independent detectors and at least one of the first detectors is sometimes referred to as "3D-GPC," while the term "GPC" alone generally refers to conventional GPC. For all absolute light scattering measurements, the 15-degree angle was used for measurement. The autosampler oven compartment was operated at 160° C. and the column compartment was operated at 150° C. The columns used were 4 Agilent "Mixed A" 30 cm 20-micron linear mixed-bed columns. The chromatographic solvent used was 1,2,4-trichlorobenzene and contained 200 ppm of butylated hydroxytoluene (BHT). The solvent source was sparged with nitrogen. The polyethylene samples were gently stirred at 160° C. for four hours. The injection volume was 200 μL. The flow rate through the GPC was set at 1 mL/minute.

The GPC column set was calibrated before running the examples by running at least twenty narrow molecular weight distribution polystyrene standards. The molecular weight (MW) of the standards ranged from 580 to 8,400,000 grams per mole, and the standards were contained in 6 "cocktail" mixtures. Each standard mixture had at least a decade of separation between individual molecular weights. The standard mixtures were purchased from Agilent Technologies. The polystyrene standards were prepared at 0.025 g in 50 mL of solvent for molecular weights equal to or greater than 1,000,000 g/mol and 0.05 g in 50 mL of solvent for molecular weights less than 1,000,000 g/mol. The polystyrene standards were dissolved at 80° C. with gentle agitation for 30 minutes. The narrow standards mixtures were run first and in order of decreasing highest molecular weight component to minimize degradation. The polystyrene standard peak molecular weights were converted to polyethylene molecular weight using Equation 2 (as described in Williams and Ward, *J. Polym. Sci., Polym. Let.*, 6, 621 (1968)):

$$M_{polyethylene} = A \times (M_{polystyrene})^B \qquad \text{(Eq. 2)}$$

where M is the molecular weight of polyethylene or polystyrene (as marked), A has a value of 0.43, and B is equal to 1.0.

A polynomial between $3^{rd}$ and $5^{th}$ order was used to fit the respective polyethylene-equivalent calibration points. The total plate count of the GPC column set was performed with Eicosane (prepared at 0.04 g in 50 mL of TCB and dissolved for 20 minutes with gentle agitation). The plate count (Equation 3) and symmetry (Equation 4) were measured on a 200 μL injection according to the following equations:

$$\text{Plate Count} = 5.54 * \left(\frac{RV_{Peak\ Max}}{\text{Peak Width at } \frac{1}{2} \text{ height}}\right)^2 \qquad \text{(Eq. 3)}$$

where RV is the retention volume in mL, the peak width is in mL, the peak max is the maximum height of the peak, and ½ height is ½ height of the peak maximum.

$$\text{Symmetry} = \frac{(\text{Rear Peak } RV_{one\ tenth\ height} - RV_{Peak\ max})}{(RV_{Peak\ max} - \text{Front Peak } RV_{one\ tenth\ height})} \qquad \text{(Eq. 4)}$$

where RV is the retention volume in mL and the peak width is in mL, Peak max is the maximum position of the peak, one tenth height is 1/10 height of the peak maximum, and where rear peak refers to the peak tail at later retention volumes than the peak max and where front peak refers to the peak front at earlier retention volumes than the peak max. The plate count for the chromatographic system should be greater than 24,000 and symmetry should be between 0.98 and 1.22.

Samples were prepared in a semi-automatic manner with the PolymerChar "Instrument Control" Software, wherein the samples were weight-targeted at 2 mg/mL and the solvent (contained 200 ppm BHT) was added to a pre-nitrogen-sparged septa-capped vial, via the PolymerChar high temperature autosampler. The samples were dissolved for 2 hours at 160° C. under "low speed" shaking.

The calculations of $Mn_{(GPC)}$, $Mw_{(GPC)}$, and $Mz_{(GPC)}$ were based on the GPC results using the internal IR5 detector (measurement channel of the PolymerChar GPC-IR chromatograph according to Equations 5-7, using PolymerChar GPCOne™ software, the baseline-subtracted IR chromatogram at each equally-spaced data collection point (i), and the polyethylene equivalent molecular weight obtained from the narrow standard calibration curve for the point (i) from Equation 2.

$$Mn_{(GPC)} = \frac{\sum^{i} IR_i}{\sum^{i} \left(IR_i / M_{polethylene_i}\right)} \qquad \text{(Eq. 5)}$$

$$Mw_{(GPC)} = \frac{\sum^{i} \left(IR_i * M_{polethylene_i}\right)}{\sum^{i} IR_i} \qquad \text{(Eq. 6)}$$

$$Mz_{(GPC)} = \frac{\sum^{i} \left(IR_i * M^2_{polethylene_i}\right)}{\sum^{i} \left(IR_i * M_{polethylene_i}\right)} \qquad \text{(Eq. 7)}$$

In order to monitor the deviations over time, a flow rate marker (decane) was introduced into each sample via a micropump controlled with the PolymerChar GPC-IR system. This flow rate marker (FM) was used to linearly correct the pump flow rate (Flowrate(nominal)) for each sample by RV alignment of the respective decane peak within the sample (RV(FM Sample)) to that of the decane peak within the narrow standards calibration (RV(FM Calibrated)). Any changes in the time of the decane marker peak are then assumed to be related to a linear-shift in flow rate (Flowrate (effective)) for the entire run. To facilitate the highest accuracy of a RV measurement of the flow maker peak, a least-squares fitting routine is used to fit the peak of the flow marker concentration chromatogram to a quadratic equation. The first derivative of the quadratic equation is then used to solve for the true peak position. After calibrating the system based on a flow marker peak, the effective flow rate (with respect to the narrow standards calibration) is calculated as Equation 8. Processing of the flow marker peak was done via the PolymerChar GPCOne™ Software. Acceptable flow rate correction is such that the effective flow rate should be within +/−2% of the nominal flow rate.

$$\text{Flowrate}_{(effective)} = \text{Flowrate}_{(nominal)} * \left(\frac{RV_{(FM\ Calibrated)}}{RV_{(FM\ Sample)}}\right) \quad \text{(Eq. 8)}$$

Triple Detector GPC (3D-GPC)

The chromatographic system, run conditions, column set, column calibration, and calculation conventional molecular weight moments and the distribution were performed according to the method described in the Gel Permeation Chromatography (GPC).

For the determination of the viscometer and light scattering detector offsets from the IR5 detector, the systematic approach for the determination of multiple detector offsets was performed in a manner consistent with that published by Balke, Mourey, et al. (Mourey and Balke, *Chromatography Polym*., Chapter 12, (1992)) (Balke, Thitiratsakul, Lew, Cheung, Mourey, *Chromatography Polym*., Chapter 13, (1992)), optimizing triple detector log ($M_w$ and intrinsic viscosity) results from a broad homopolymer polyethylene standard (Mw/Mn>3) to the narrow standard column calibration results from the narrow standards calibration curve using PolymerChar GPCOne™ Software.

The absolute molecular weight data was obtained in a manner consistent with that published by Zimm (Zimm, B. H., *J. Chem. Phys.*, 16, 1099 (1948)) and Kratochvil (Kratochvil, P., *Classical Light Scattering from Polymer Solutions*, Elsevier, Oxford, NY (1987)). The overall injected concentration used in the determination of the molecular weight is obtained from the mass detector area and the mass detector constant derived from a suitable linear polyethylene homopolymer, or one of the polyethylene standards of known weight-average molecular weight. The calculated molecular weights (using GPCOne™) are obtained using a light scattering constant derived from one or more of the polyethylene standards mentioned and a refractive index concentration coefficient, dn/dc, of 0.104. Generally, the mass detector response (IR5) and the light scattering constant (determined using GPCOne™) should be determined from a linear standard with a molecular weight in excess of about 50,000 g/mol. The viscometer calibration (determined using GPCOne™) can be accomplished using the methods described by the manufacturer or alternatively by using the published values of suitable linear standards such as Standard Reference Materials (SRM) 1475a (available from National Institute of Standards and Technology (NIST)). A viscometer constant (obtained using GPCOne™) is calculated which relates specific viscosity area (DV) and injected mass for the calibration standard to its intrinsic viscosity. The chromatographic concentrations are assumed low enough to eliminate addressing $2^{nd}$ viral coefficient effects (concentration effects on molecular weight).

The absolute weight average molecular weight ($Mw_{(Abs)}$) is obtained (using GPCOne™) from the Area of the Light Scattering (LS) integrated chromatogram (factored by the light scattering constant) divided by the mass recovered from the mass constant and the mass detector (IR5) area. The molecular weight and intrinsic viscosity responses are linearly extrapolated at chromatographic ends where signal to noise becomes low (using GPCOne™). Other respective moments, $Mn_{(Abs)}$ and $Mz_{(Abs)}$ are calculated according to equations 9-10 as follows:

$$Mn_{(Abs)} = \frac{\sum^{i} IR_i}{\sum^{i} \left(IR_i / M_{Absolute_i}\right)} \quad \text{(Eq. 9)}$$

$$Mz_{(Abs)} = \frac{\sum^{i} \left(IR_i * M^2_{Absolute_i}\right)}{\sum^{i} \left(IR_i * M_{Absolute_i}\right)} \quad \text{(Eq. 10)}$$

Fourier Transform Infrared Analysis

Sample films (approximately 250-300 microns in thickness) used for Fourier-Transform Infrared (FTIR) analysis were compression molded by pressing approximately 0.5 g of pellets of the sample in a Carver hydraulic press with heated platens set to 190° C.

High Temperature Liquid Chromatography (HTLC)

High temperature liquid chromatography (HTLC) was employed for separation and characterization of Si-PE hybrid. Free PDMS was quantified by external standard calibration method. Sample solutions were prepared at ~2.0 mg/mL in anhydrous decane. Samples were dissolved using a lab heated shaker at 130° C. for ~1 hour. After that the sample solution was transferred to the PolymerChar autosampler. The sample solution was re-heated and shaken at 130° C. by the heated shaker in PolymerChar for 1 hour prior to injection. HTLC was based on the PolymerChar high temperature 2DLC/GPC instrument. LC pump was an Agilent 1260 HPLC system that was set a flow rate of 1.0 mL/min. Injection loop was a 20 μL of solution. A ThermoFisher hypercarb column (4.6 mm i.d.×100 mm 1., 5 um particle size and 260 Å pore size) held at 130° C. was used for the separation. The detector was an Agilent HT-ELSD detector (model G7826A) with the settings of nebulizer temperature 160° C.; evaporator temperature 120° C. and $N_2$ flow at 0.2 SLM. The gradient of decane to ODCB was applied in the separation according to Table 1. The data were collected by PolymerChar software version 1.1, and was reduced by Agilent SEC software Cirrus 3.3.

TABLE 1

| Gradient table | | |
|---|---|---|
| time | n-decane | ODCB |
| 0 | 100 | 0 |
| 10 | 100 | 0 |
| 20 | 0 | 100 |
| 25 | 0 | 100 |
| 30 | 100 | 0 |

Nuclear Magnetic Resonance (NMR)

The samples were prepared by adding 0.1 to 0.2 g of sample to 3.25 g of 50/50 by weight Tetrachlorethane-d2/Perchloroethylene with 0.001 M $Cr(AcAc)_3$ in a Norell 1001-7 10 mm NMR tube. The samples were purged by bubbling $N_2$ through the solvent via a pipette inserted into the tube for approximately 5 minutes to prevent oxidation, capped, and sealed with Teflon tape. The samples were heated and vortexed at 115-135° C. to ensure homogeneity. $^1H$ NMR was performed on a Bruker AVANCE 600 MHz spectrometer equipped with a Bruker 10 mm CryoProbe and a sample temperature of 120° C. The spectra were acquired with ZG pulse, 16 scans, AQ 1.8 s, $D_1$ 14 s. The polymer integral from about 0.6 to 2.6 ppm was set to an arbitrary value. This value divided by 2 gives the total moles of polymer $CH_2$s. Total moles $CH_2$ multiplied by 14 g/mol gives the polymer weight. The PDMS integral from about −0.3 to 0.6 ppm divided by 6 gives moles PDMS units. Multiplying by 74.1 g/mol PDMS unit gives the PDMS weight. The two weights are used to calculate wt % PDMS.

Peel Force

The peel force required to remove a feminine hygiene pad from the release layer of a multilayer film pouch wrap, according to one or more embodiments, is measured by the following method. The release layer of a multilayer film was placed in contact with the adhesive layer of a commercially available feminine hygiene pad ("Salvaslip EVAX Normal" from The Procter and Gamble Company). The feminine hygiene pad and multilayer film were placed in an oven for 20 hours at 40° C. under a 2 kg weight. The feminine hygiene pad and multilayer film were removed from the oven and were kept at room temperature for 4 hours. Peel force was measured by a 25 mm×175 mm probe with a 10 N cell using a speed of 300 mm/min, a grip distance of 25 mm and a measurement distance of 100 mm at 90°.

Coefficient of Friction

Coefficient of friction is measured according to ISO-8295, placing the release layer of the pouch wrap on the inside.

EXAMPLES

The following examples illustrate features of the present disclosure but are not intended to limit the scope of the disclosure. The following experiments analyzed the performance of embodiments of the multilayer films described herein.

Example 1—Production of PDMS-co-LDPE

The f-PDMS was formed as a 1:2:1 mixture of the following three siloxanes:

methacrylate functionalized PDMS MW = 15K

| F-PDMS | ratio |
| --- | --- |
| 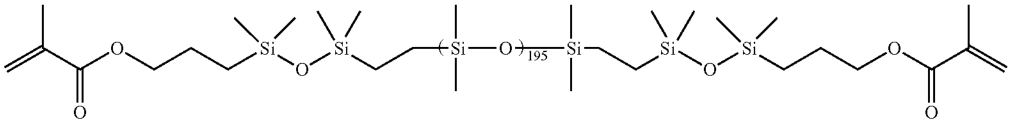 [SMILES: C=C(C)C(=O)OCCC[Si](C)(C)O[Si](C)(C)CC[Si](C)(C)O[Si](C)(C)CC[Si](C)(C)O[Si](C)(C)CCCOC(=O)C(=C)C] | 1 |
| 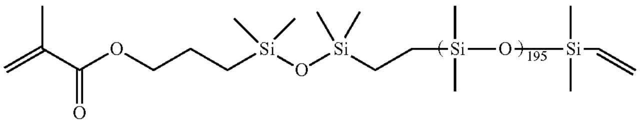 [SMILES: C=C[Si](C)(C)O[Si](C)(C)CC[Si](C)(C)O[Si](C)(C)CCCOC(=O)C(=C)C] | 2 |
| 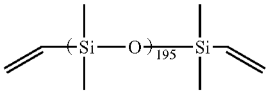 | 1 |

Polymerization was carried out in a continuously stirred tank reactor (CSTR) with a volume of 300 mL heated to 220° C. using four electric heater bands. The agitator speed was 1800 revolutions per minute (RPM). The reactor pressure was controlled to approximately 193 MPa. Propylene was used as a chain transfer agent. Ethylene and propylene were fed to the top of the reactor along the agitator shaft at a flow rate of 5440-5470 g/h ethylene in the ratios reported in Table 1, below. TPA and TPO were used as initiators in a 0.61:1 mass ratio. The initiators were diluted in ISOPAR E (available from ExxonMobil Chemical Co.) and injected into the side of the reactor at a pressure of 193 MPa at a ratio of 30-33 mass ppm TPA and 50-54 mass ppm TPO to ethylene. The f-PDMS was diluted in ethyl acetate (available from Sigma Aldrich) to 30 wt % and separately injected into the side of the reactor at a flow rate as reported in Table 1, below.

The reactor residence time was about 1.5 minutes. All unreacted reactants and polymer were emitted via a single outlet located on the bottom of the reactor. The PDMS-co-LDPE polymer was then separated from the remaining reactants by atomization, depressurizing the stream to about 0.1 MPa and simultaneously cooling the stream to ambient temperatures. The PDMS-co-LDPE polymer was then collected in powder form.

The amount of both attached and unattached PDMS in sample 1 was estimated by HNMR and showed 7.77 wt % of PDMS in the resin.

The amount of unattached (free) f-PDMS in PDMS-co-LDPE resin was estimated using HTLC analysis. Average value from two repetitions for Sample 1 was 3.0 wt % of unattached PDMS in a resin that corresponds to 61.4% conversion of the added f-PDMS to PDMS-co-LDPE.

The process conditions by which the PDMS-co-LDPE polymer (Sample 1) was made are reported in Table 2.

TABLE 2

| | Reaction Temp. (° C.) | Ethylene Conversion (wt %) | Propylene/ Ethylene (mol ppm) | f-PDMS/ Ethylene (mass ppm) | Avg. Melt Index at 190° C. ($I_2$) (dg/min) |
|---|---|---|---|---|---|
| Comparative Sample A (no f-PDMS) | 220.89 | 11.29 | 24900 | 0 | 2.9 |
| Sample 1 (7.77 wt % f-PDMS) | 217.48 | 11.56 | 29600 | 13210 | 1.9 |

Figure 4A:
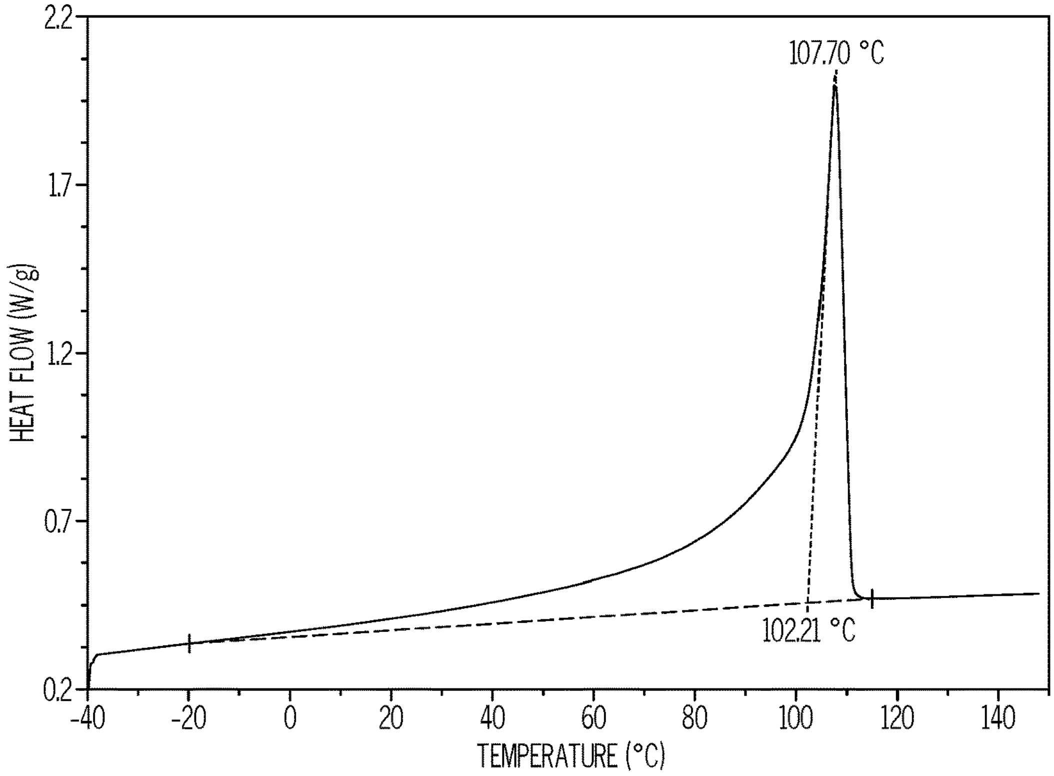
FIG. 4A is a differential scanning calorimetry (DSC) second heating curve of an example PDMS-co-LDPE according to one or more embodiments shown and described herein.
Figure 4B:
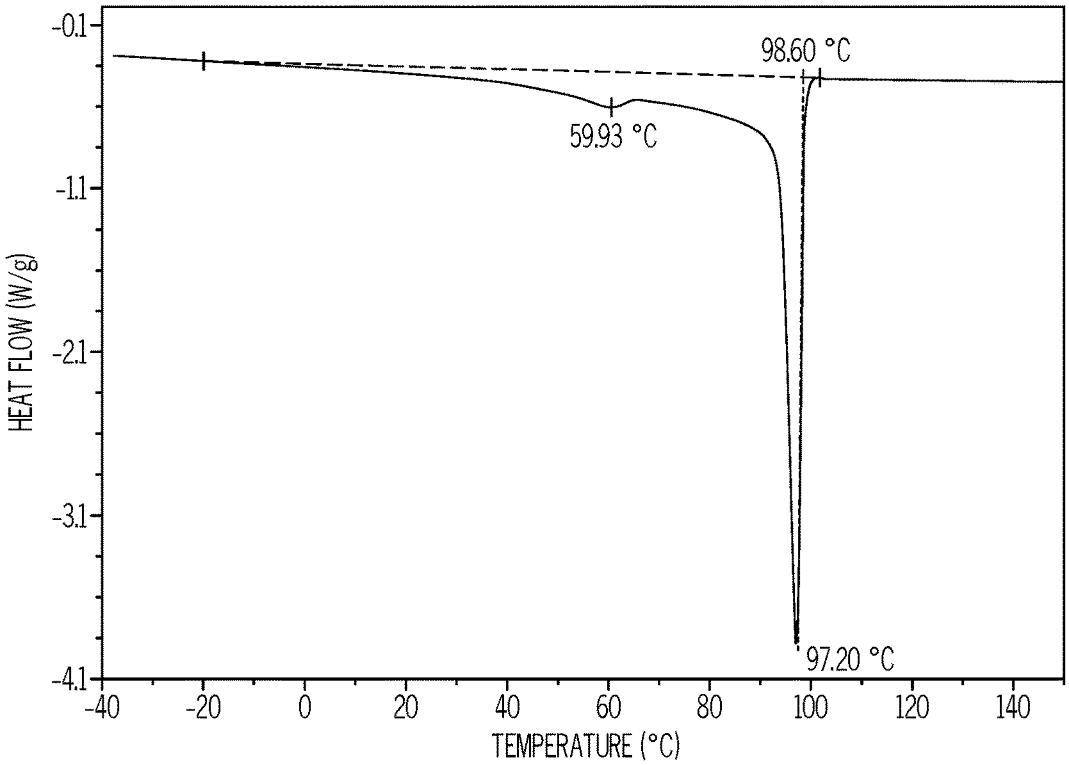
FIG. 4B is a DSC cooling curve of an example PDMS-co-LDPE according to one or more embodiments shown and described herein.

DSC analysis of the PDMS-co-LDPE of Sample 1 was performed and the results are provided in FIGS. 4A and 4B. The data shown in FIGS. 4A and 4B shows a melting temperature of 107.7° C. (FIG. 4A) and a heat of fusion of 136.1 J/g (FIG. 4B).

Figure 5:
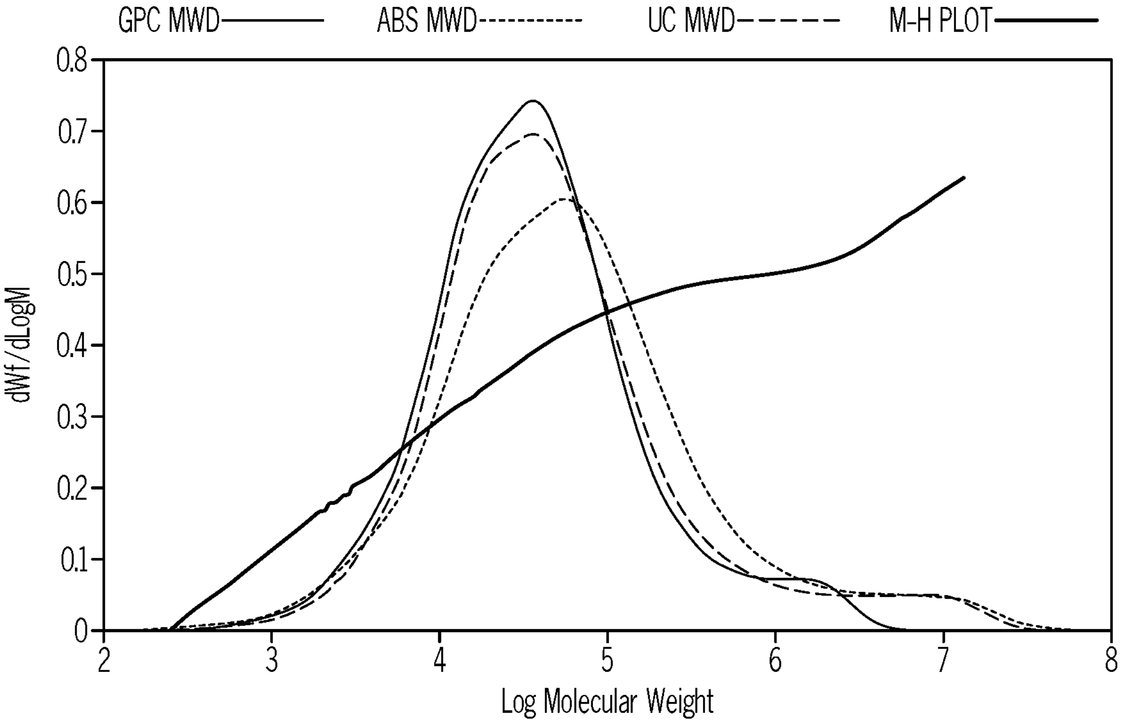
FIG. 5 is a plot of the molecular weight distribution obtained from gel permeation chromatography (GPC) analysis of an example PDMS-co-LDPE according to one or more embodiments shown and described herein.

Sample 1 was additionally analyzed using conventional GPC and 3D-GPC. Table 3 reports the molecular weight properties for the sample. The molecular weight distribution is plotted in FIG. 5.

TABLE 3

| Molecular Weight Properties | | | |
|---|---|---|---|
| Conventional GPC | | Absolute GPC (3D-GPC) | |
| Mr | 14,600 | Mn | 15,540 |
| Mp | 35,990 | Mw | 601,010 |
| Mv | 91,880 | Mz(BB) | 1,883,550 |
| Mw | 136,800 | Mz(abs) | 12,832,240 |
| Mz | 1,271,320 | Mz + 1(BB) | 2,952,220 |
| PDI | 9.37 | Mz/Mw | 21.35 |

Figure 6A:
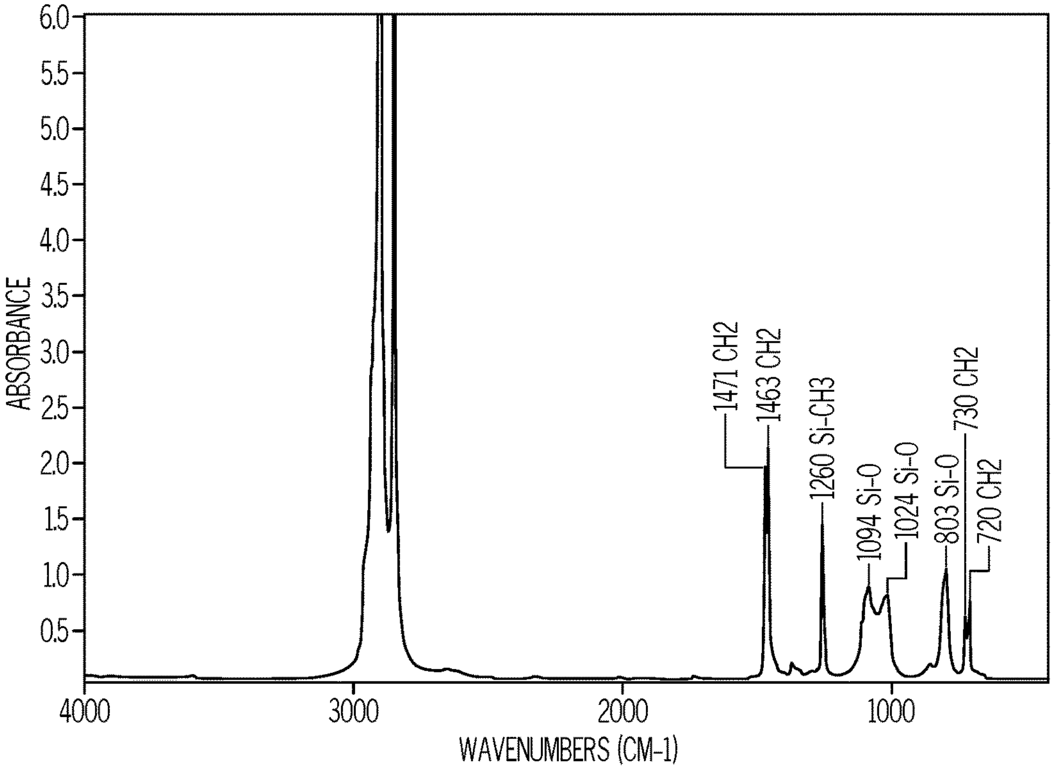
FIG. 6A is an FTIR spectrum for an example PDMS-co-LDPE according to one or more embodiments shown and described herein.
Figure 6B:
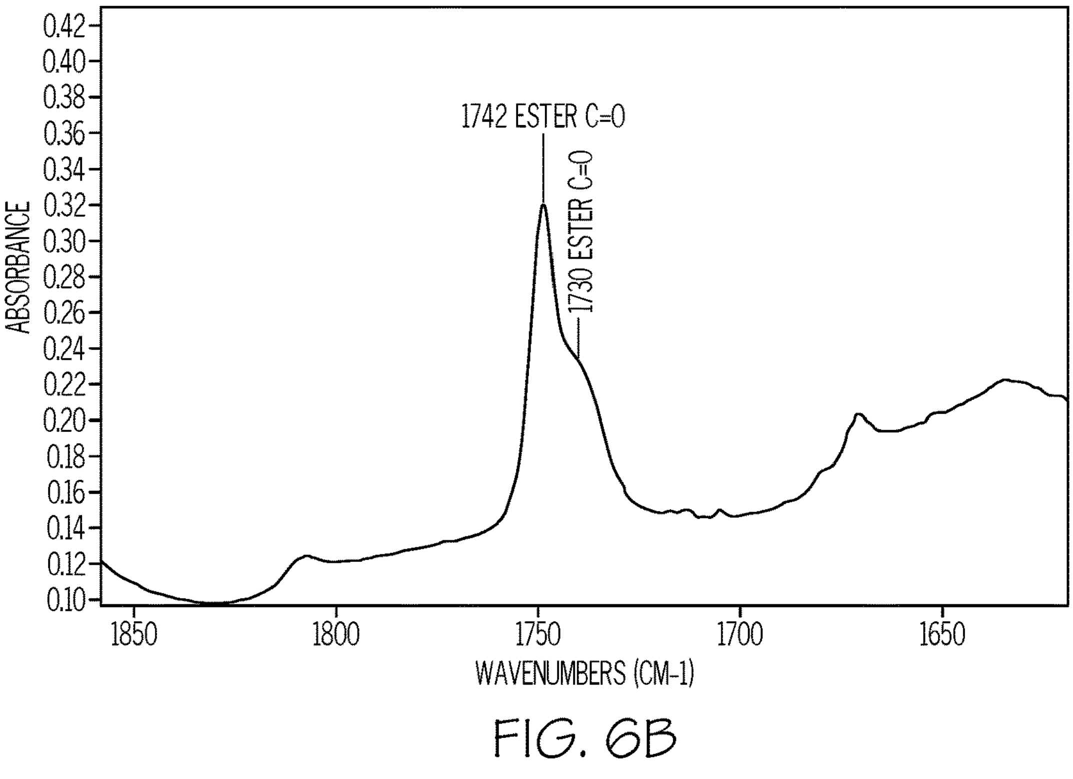
FIG. 6B is a close up of the FTIR spectrum of FIG. 6A from about 1850 to about 1600 cm−1.

Sample 1, prepared as described hereinabove, was further analyzed using IR spectroscopy. The spectra for PDMS-co-LDPE are presented in FIG. 6A, and FIG. 6B showing additional detail from FIG. 6A from about 1850 to about 1600 $cm^{-1}$. In the IR spectra, peaks corresponding to LDPE and PDMS are shown. A peak at 1742 $cm^{-1}$ corresponds to ethylacetate that was used as a solvent to add functional PDMS. A peak at 1730 $cm^{-1}$ is present corresponding to the ester function of the copolymerized methacrylate functional group.

Example 2—Production of Multilayer Films

Two multilayer films were produced by extrusion to form Sample 2 and Sample 3. Each multilayer film included two substrate layers (A and B) and one functional layer (C). The substrate layers were 70% DOWLEX™ 2042EC and 30% LDPE 310E. DOWLEX™ 2042EC is a linear low density polyethylene (LLDPE) commercially available from The Dow Chemical Company and has a melt flow index (MFI) of 1 g/10 min (measured at 190° C. and 2.16 kg) and a density of 0.930 $g/cm^3$. LDPE 310E is also commercially available from The Dow Chemical Company and has a MFI of 0.75 g/10 min (measured at 190° C. and 2.16 kg) and a density of 0.923 $g/cm^3$. The functional layer of Sample 2 was LDPE 310E, and the functional layer of Sample 3 was the PDMS-co-LDPE of Example 1. The composition of the multilayer films of Samples 2 and 3 are summarized in Table 4.

TABLE 4

| Sample | Substrate Layers (A and B) | Functional Layer (C) |
|---|---|---|
| Sample 2 | 70% DOWLEX ™ 2042EC + 30% LDPE 310E | LDPE 310E |
| Sample 3 | 70% DOWLEX ™ 2042EC + 30% LDPE 310E | PDMS-co-LDPE of Example 1 |

Samples 2 and 3 were produced by blown film extrusion. The film layer distribution was 10 wt % A, 80 wt % B, and 10 wt % C and the total film thickness of each multilayer film was 20 microns. The blow up ratio during extrusion was 1:2.5 and the die gap was 1.8 mm. The melt temperature for the functional layers of Samples 2 and 3 was 175° C., and the melt temperature for the substrate layer of each multilayer film was 230° C. The output rate of the extruder was 12 kg/hr.

Example 3—Coefficient of Friction Measurements

The static and dynamic coefficients of friction (COF) of Samples 2 and 3 of Example 2 were measured according to ISO-8295 where the functional layer of each multilayer film was the inside layer. The coefficient of friction results are displayed in Table 5.

TABLE 5

| Sample | Static COF | Std. Dev. | Dynamic COF | Std. Dev. |
|---|---|---|---|---|
| Sample 2 | 0.61 | 0.04 | 0.64 | 0.03 |
| Sample 3 | 0.37 | 0.02 | 0.30 | 0.01 |

Sample 2 of Example 2 exhibited a high static coefficients of friction of 0.61 and a high dynamic coefficient of friction of 0.64. Sample 3 of Example 2 had lower static and dynamic coefficients of friction (0.37 and 0.30 respectively) than the Samples 2 of Example 2. Thus, the Sample 3 of Example 2 is more suitable for use in packaging feminine hygiene pads.

Example 4—Peel Strength Measurements

The maximum peel force and average peel force required to remove a feminine hygiene pad from each of Samples 2 and 3 of Example 2 were determined by the above described testing method. The maximum and average peel forces required to remove a feminine hygiene pad from each of Samples 2 and 3 of Example 2 are displayed in Table 6.

TABLE 6

| Sample | Max. Peel Force (N/25 mm) | Std. Dev. | Avg. Peel Force (N/25 mm) | Std. Dev. |
|---|---|---|---|---|
| Sample 2 | 8.0 | 0.6 | 2.9 | 0.5 |
| Sample 3 | 3.8 | 0.2 | 1.6 | 0.1 |

Sample 2 of Example 2 exhibited a high maximum peel force of 8.0 N/25 mm and high average peel force of 2.9 N/25 mm. Sample 3 of Example 2 exhibited a maximum peel force of 3.8 N/25 mm and an average peel force of 1.6 N/25 mm. Sample 3 exhibited over a 50% reduction in maximum peel force and almost a 50% reduction in average peel force over Sample 2 of Example 2. Thus, Sample 3 of Example 2 is more suitable for use in pouch wrap packaging for feminine hygiene articles.

It will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these aspects.

The invention claimed is:

1. A feminine hygiene article comprising:

a feminine hygiene pad comprising an absorbent body and an adhesive layer positioned on at least a surface of the absorbent body; and a pouch wrap in contact with the adhesive layer of the feminine hygiene pad, the pouch wrap comprising a release layer in direct contact with the adhesive layer, the release layer comprising a polymer composition comprising low density polyethylene covalently bonded to polydimethylsiloxane;

wherein the polymer composition comprises the reaction product of the copolymerization of ethylene and (meth) acrylic ester functionalized polydimethylsiloxane; and wherein the reaction product of the copolymerization of ethylene and (meth)acrylic ester functionalized polydimethylsiloxane comprises one or more of the following structures:

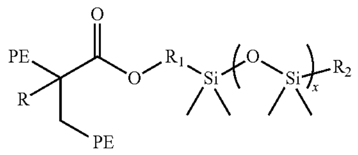

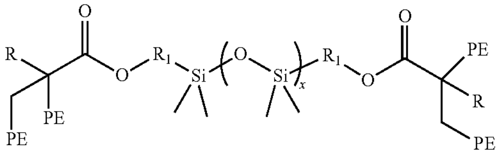

and

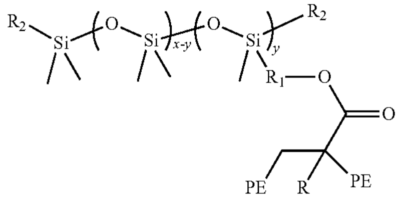

where R is a methyl group or a hydrogen, $R^1$ is a bridge group that connects functional group ((meth)acrylate) with siloxane, $R^2$ is an end group selected from the group consisting of alkyl, substituted alkyl, aryl, alkenyl, H, and OH, x is an integer from 10 to 1000, and y is an integer from 1 to 20.

2. The feminine hygiene article of claim 1, wherein the polymer composition comprises low density polyethylene covalently bonded to the polydimethylsiloxane by one or more $CH_2$ groups, wherein the one or more $CH_2$ groups are former methyl groups of the polydimethylsiloxane.

3. The feminine hygiene article of claim 2, wherein the polymer composition comprises low density polyethylene covalently bonded to the polydimethylsiloxane by one or more $CH_2$ groups, wherein the one or more $CH_2$ groups are former methyl groups of the polydimethylsiloxane and wherein the polymer composition has a density from 0.91 g/cc to 0.99 g/cc.

4. The feminine hygiene article of claim 1, wherein the pouch wrap has a basis weight from 5 to 40 gsm.

5. The feminine hygiene article of claim 1, wherein the pouch wrap further comprises one or more support layers comprising one or more polymers, wherein the release layer is positioned between the one or more support layers and the adhesive layer.

6. The feminine hygiene article of claim 5, wherein the release layer comprises 5 wt % to 20 wt % of the pouch wrap.

7. The feminine hygiene article of claim 5, wherein the one or more support layers comprises low density polyethylene, linear low density polyethylene, medium density polyethylene, high density polyethylene, ultra low density polyethylene, or combinations of these.

8. The feminine hygiene article of claim 5, wherein the pouch wrap comprises from 2 to 8 support layers.

9. The feminine hygiene article of claim 5, further comprising a nonwoven fabric layer, wherein the one or more support layers are positioned between the nonwoven fabric layer and the release layer.

10. The feminine hygiene article of claim 1, wherein the pouch wrap is void of any materials comprising at least 60 wt % silicone resins.

11. The feminine hygiene article of claim 1, wherein one or more of:

a maximum peel force of at most 7.0 N/25 mm is required to remove the feminine hygiene pad from the pouch wrap; or a static coefficient of friction of the release layer is at most 0.55 and a dynamic coefficient of friction of the release layer is at most 0.60.

12. A multilayer film structure comprising:

one or more support layers comprising polymers; and a release layer in direct contact with a support layer, the release layer comprising a polymer composition comprising ethylene and (meth)acrylic ester functionalized polydimethylsiloxane copolymers;

wherein the polymer composition comprises the reaction product of the copolymerization of ethylene and (meth) acrylic ester functionalized polydimethylsiloxane, wherein the ethylene and (meth)acrylic ester functionalized polydimethylsiloxane comprises one or more of the following structures:

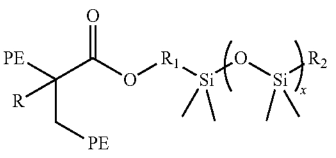

-continued

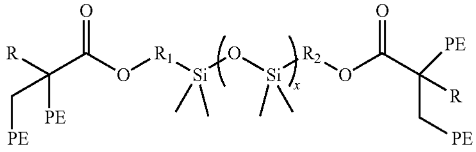

and

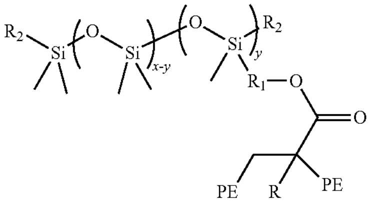

where R is a methyl group or a hydrogen, $R^1$ is a bridge group that connects functional group ((meth)acrylate) with siloxane, $R^2$ is an end group selected from the group consisting of alkyl, substituted alkyl, aryl, alkenyl, H, and OH, x is an integer from 10 to 1000, and y is an integer from 1 to 20.

13. The multilayer film structure of claim 12, further comprising an adhesive layer in direct contact with the release layer.

* * * * *